(12) United States Patent
Burgi

(10) Patent No.: US 8,236,003 B2
(45) Date of Patent: Aug. 7, 2012

(54) PROSTHESIS COMPONENT HOLDER ATTACHABLE TO AN INSERTER HANDLE

(75) Inventor: Jonas Burgi, Moutier (CH)

(73) Assignee: Greatbatch Medical S.A., Orvi (CH)

( * ) Notice: Subject to any disclaimer, the term of this patent is extended or adjusted under 35 U.S.C. 154(b) by 1040 days.

(21) Appl. No.: 11/954,379

(22) Filed: Dec. 12, 2007

(65) Prior Publication Data

US 2008/0154261 A1   Jun. 26, 2008

Related U.S. Application Data

(60) Provisional application No. 60/871,300, filed on Dec. 21, 2006.

(51) Int. Cl.
*A61F 2/46* (2006.01)
(52) U.S. Cl. ............................................ 606/91; 606/99
(58) Field of Classification Search .................. 606/91, 606/80–81, 79, 99
See application file for complete search history.

(56) References Cited

U.S. PATENT DOCUMENTS

| 5,980,170 A * | 11/1999 | Salyer ..................... 408/239 R |
| 2004/0186586 A1* | 9/2004 | Seyer et al. ................. 623/22.12 |
| 2006/0149270 A1* | 7/2006 | Myers ............................. 606/81 |
| 2006/0241781 A1* | 10/2006 | Brown et al. ............... 623/23.43 |

* cited by examiner

*Primary Examiner* — Kevin T Truong
*Assistant Examiner* — Larry E Waggle, Jr.
(74) *Attorney, Agent, or Firm* — Michael F. Scalise

(57) ABSTRACT

An adaptor/holder (40) is described which attaches to the front (18) of an existing orthopedic inserter/impactor handle (10) via the handle's existing threaded interface mechanism (22). The adaptor/holder (40) has an annular housing (42) that snaps onto the front (18) of the existing inserter (10), and has an internal yoke and pin assembly (70) that attached to the handle's interface mechanism (22). The holder (40) adapts the inserter (10) to much more easily and quickly release from a prosthetic component (12) after the component (12) is surgically implanted in a patient, and with less mechanical manipulation than could otherwise be accomplished using the inserter (10) alone. The adaptor/holder utilizes the inserter's existing mount tensioning (draw piston) mechanism (30) to quickly engage and disengage the prosthetic component (12). Upon activation of the inserter's tensioning mechanism (30), the holder (10) receives and fixes a prosthetic component (12) to the end (18) of the inserter (10). Deactivation of the inserter handle's tensioning mechanism (30) quickly accomplishes release of the prosthetic component (12) with minimal manipulation.

23 Claims, 8 Drawing Sheets

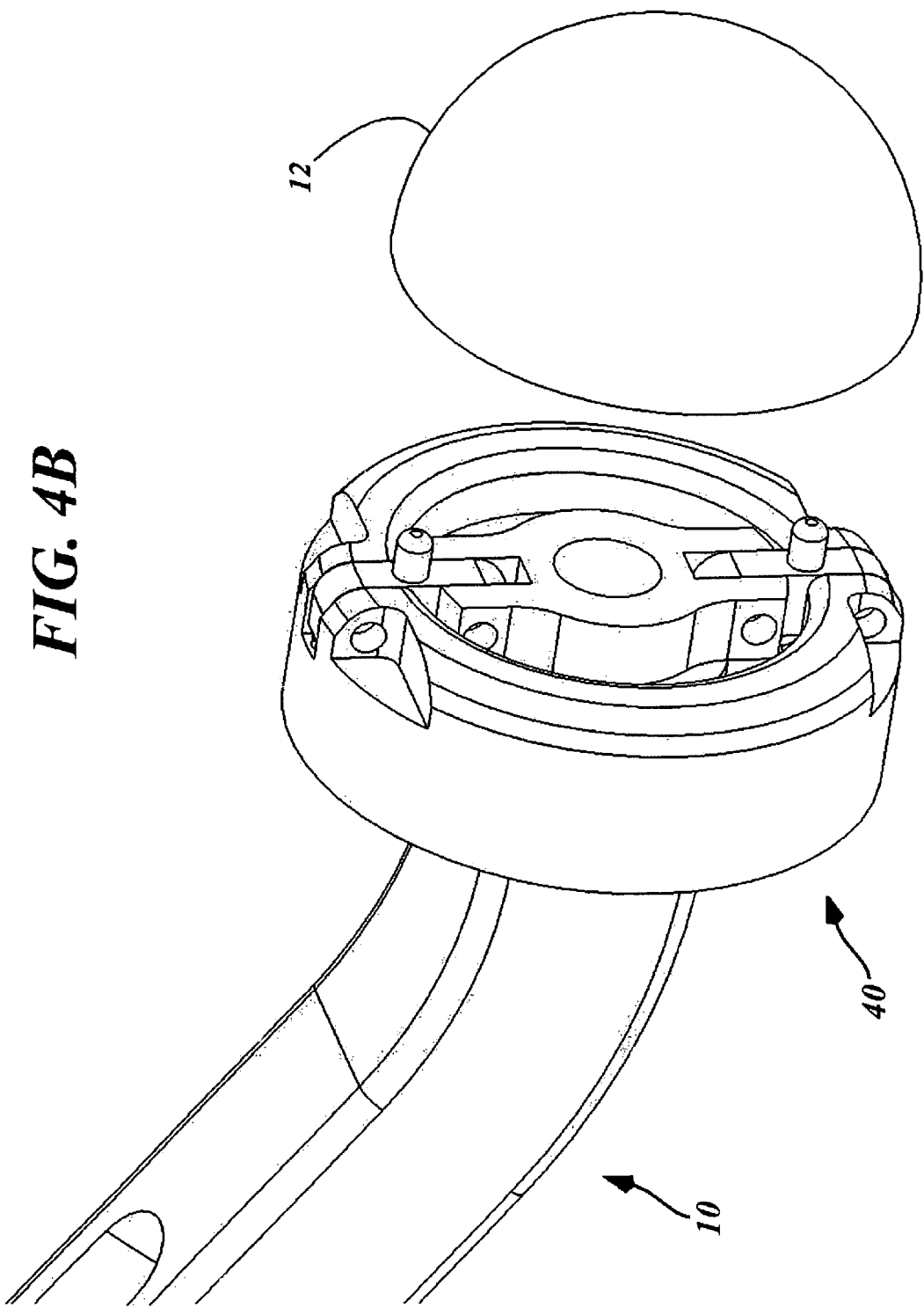

PROSTHESIS COMPONENT HOLDER ATTACHABLE TO AN INSERTER HANDLE

The present application claims the benefit of prior filed U.S. Provisional Patent Application Ser. No. 60/871,300 filed 24 Dec. 2006, the content of which is incorporated herein by reference.

FIELD OF THE INVENTION

The present invention is in the field of orthopedic surgical instrumentation (class 606/53). Specifically, the present invention relates to surgical instrumentation for use in bone preparation for the manipulation, placement or removal of an internal bone prosthesis (class 606/53; 86). More specifically, the present invention relates to prosthesis inserters, such as impactors, adapted to place or remove a bone repairing means through forceful contact, in which momentum is transferred from the force transferring means to the preparation means (class 606/53; 86; 99).

BACKGROUND OF THE INVENTION

Surgical procedures for the implantation of orthopedic prosthetic assemblies often requires specialized tools specifically adapted for insertion of a particular component of the prosthetic assembly. In the field, a number of different inserter handles for use in a surgical procedure to hold and manipulate a prosthesis component during its implantation in a patient are described. Typically, inserter handles have a front end (mount end) adapted to receive and hold a particular prosthesis component during implantation, and to release the component upon completion of its installation. An example of such an existing inserter handle is described in WIPO Publication Number WO 2005/044153 to Lechot & Desarzens, the content of which is incorporated herein by reference.

In this type of inserter handle, the mount end is adapted to releasably mate with a prosthesis component via a threaded interface. The action for achieving the threaded interface between the mount and the component of the prosthetic assembly is accomplished using a screw knob disposed at the impactor end of the inserted handle. Rotating the screw knob rotates the threaded interface at the mount end of the inserter handle to securely engage or disengage the prosthetic component. In practice, the prosthetic component is first securely screwed to the mount end of the inserter handle by the user rotating the screw knob. The combination of the inserter handle with the prosthetic component attached is used to seat the prosthetic component at its intended implantation site in the patient utilizing the impactor feature/function of the inserter handle. Once the prosthetic component is seated in a proper relationship in the installation site in the patient, the user counter-rotates the screw knob to disengage the threaded interface of the mount end from the prosthetic component, and the inserter handle is removed from the patient leaving the component in situ.

A disadvantage of this practice is that, once the proper relationship of the prosthetic component is achieved in the installation site, it is necessary as well to hold the positional relationship of the inserter handle relative to the installation site during the disengagement of the threaded interface of the mount end from the prosthetic component. Holding this positional relationship during disengagement can be problematic (e.g., because of the relatively substantial mass and length of the inserter handle, the time and amount of manipulation required to reverse the securely threaded interface, etc.). Therefore, it would be advantageous to the field to have an interface between the inserter handle and the prosthetic component that is quickly disengageable and requires little manipulation to accomplish. Additionally, it would be beneficial to have an interface that could accommodate a variety of prosthetic component configurations for combination with a given inserter handle.

SUMMARY OF THE INVENTION

The present invention is a mount adaptor/holder that is attachable to the mount end of an existing inserter handle, which adapts the inserter handle to quickly engage and disengage a component of an orthopedic prosthesis assembly. An example of an orthopedic prosthesis assembly is an artificial ball and rotator cup joint, comprising a ball prosthetic component receivable in a rotator cup prosthetic component. Such orthopedic prosthesis joint assemblies are known in the art.

The present adaptor/holder is designed to attach to the mount (or tool) end of an inserter handle via an existing threaded interface mechanism of the handle. The adaptor/holder then utilizes the inserter handle's existing mount tensioning mechanism to accomplish the quick engagement and disengagement of a component of an orthopedic prosthesis assembly. Upon activation of the inserter handle's tensioning mechanism, the adaptor mount receives and fixes a prosthetic component to the tool end of the inserter handle for use. Deactivation of the inserter handle's tensioning mechanism is quickly accomplished with minimal manipulation to rapidly release the prosthetic component. In the cases illustrated herein, the prosthetic component to be installed is a cup insert.

An important feature of the present prosthetic component holder is that it enables the prosthetic component to be detached from the inserter handle, in situ, without having to operate the drive assembly of the handle to release the component after its installation in a patient. This feature of the present holder and handle combination eliminates the need for a threaded interface on the prosthetic component. A benefit of this feature is that, unlike prior inserter devices, the entire instrument (the handle with the holder still attached) can be quickly removed from the surgical site without having to maintain the positioning of the handle relative to the prosthetic component (e.g., an insert cup) inside the patient. That is done by unscrewing the drive linkage assembly to separate the handle from the insert cup. Additionally, in prior inserter handles, where the inserted cup is screwed to the tool end of the drive linkage, unscrewing the drive linkage assembly can apply rotational torque to the installed prosthesis cup, which can potentially cause the cup to move from its set position or even to become dislodged.

BRIEF DESCRIPTION OF THE DRAWINGS

FIG. 4B is a perspective view of the present holder mounted to the tool end of an inserter handle with a prosthetic cup insert positioned to be attached to the holder before actuation of the holder, and showing the normal relationship of the component parts of the holder.

DETAILED DESCRIPTION OF THE INVENTION

Figure 1:
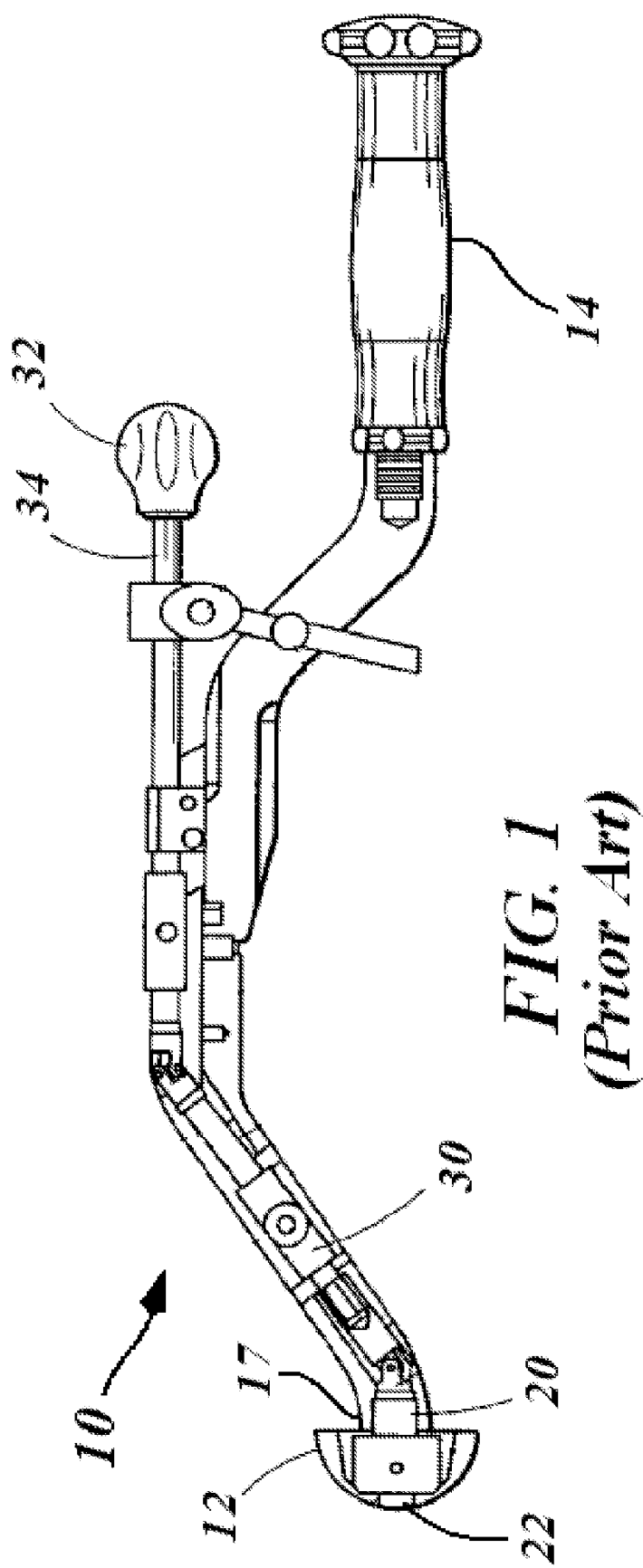
FIG. 1 is a side view of a prior impactor-type inserter handle with a prosthetic component mounted on its front end.

Referring now to the drawings, the details of preferred embodiments of the present invention are graphically and schematically illustrated. Like elements in the drawings are represented by like numbers, and any similar elements are represented by like numbers with a different lower case letter suffix.

Figure 2:
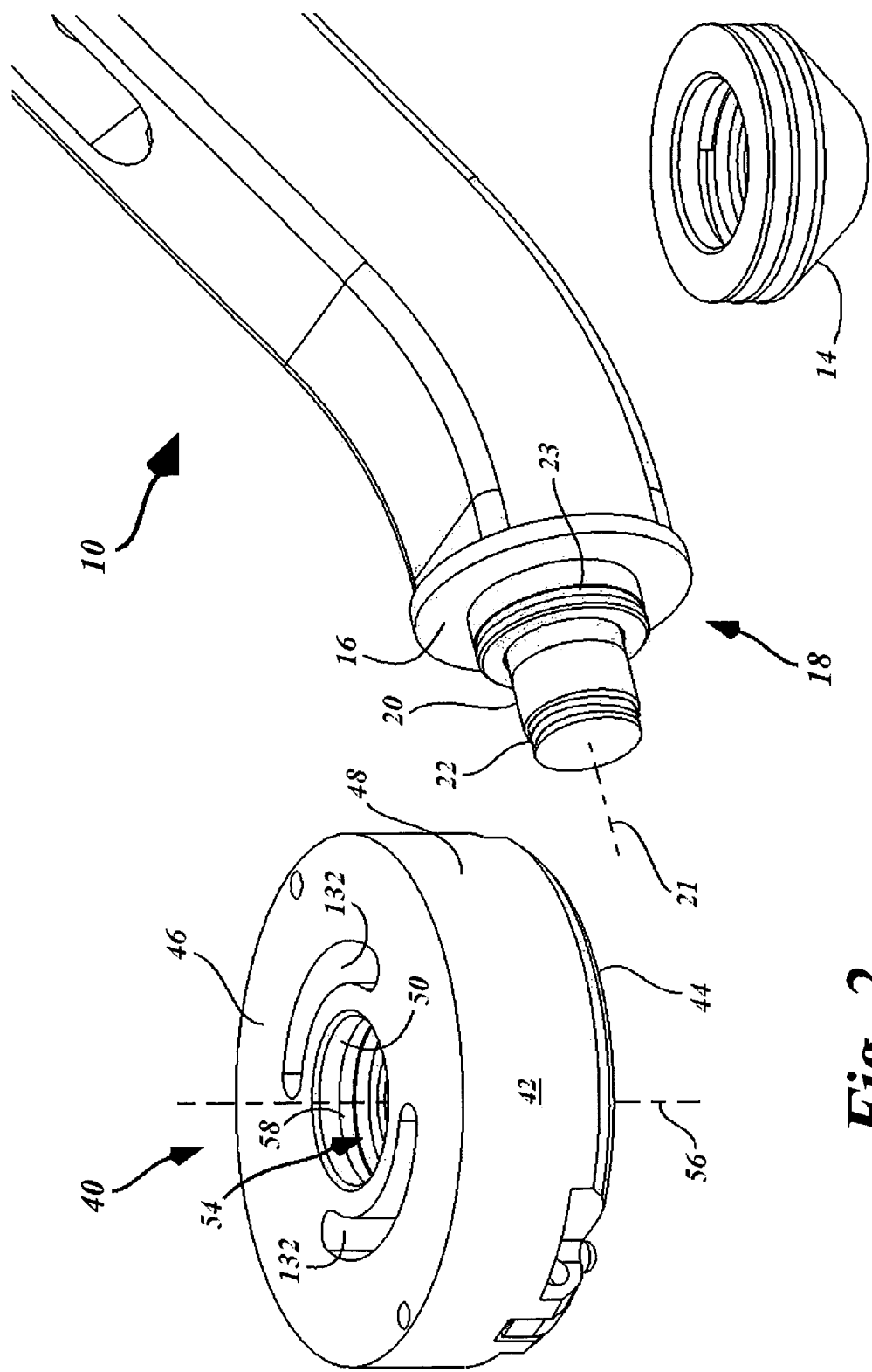
FIG. 2 is a perspective drawing showing the tool attachment end of an inserter handle, the attachment end being able to mount an interchangeable nose or the prosthesis component holder of the present invention.

As shown in FIG. 2, the present invention is a prosthesis component holder 40 attachable to the mount/tool end 17 of an existing inserter handle 10 (see FIG. 1). The inserter handle 10 has a draw piston 20 projecting through the drive end boss 18 at its mount end 17. The draw piston 20 is operated by the lever action of the drive chain shaft 34 of the handle 10. The holder 40 comprises an annular housing 42 attachable to the drive end boss 18 of the inserter handle 10. The housing 42 has several surfaces including: a front surface 44, a back surface 46, an outer surface 48 and an inner surface 50. The inner housing surface 50 defines an annular opening 54 in the housing 42. The annular opening 54 has a central annulus axis 56

As also illustrated in FIG. 2, an attachment mechanism 58 is disposed on the inner surface 50 of the housing 42 proximate the back surface 46. The attachment mechanism 58 is disposed to mate with a complimentary mating mechanism 23 at the drive end boss 18 (see FIG. 3). The attachment mechanism 58 releasably attaches the present holder 10 to the drive end boss 18 of the handle 40, so that back surface 46 of the housing 42 contacts the attachment interface 16 of the drive end boss 18. In the embodiment illustrated, the attachment mechanism 58 comprised a circumferential groove 60 on the inner surface 50 of the housing 42 proximate the back surface 46, into which groove 60 a snap-ring 62 was received. The complimentary mating mechanism 23 on the drive end boss 18 is a complementary circumferential detent groove on the barrel 26 of the drive end boss 18. Other complementary mechanisms 58 and 23 are known to and selectable by the ordinary skilled artisan for practice in the present invention. For example, a pin and "J"-groove or bayonet mechanisms can be used. However, the snap-ring and detent combination illustrated for attaching the holder 40 to the drive end boss 18 has the advantage, as explained later, of allowing the holder to be rotationally oriented on the drive end boss 18 after attachment.

A cavity 66 is set into the front housing surface 44 of the housing 42. The cavity 66 communicates with the annular opening 54, and is a widening of the annular opening 54 disposed to receive the coupling mechanism 70 of the holder 40. The coupling mechanism 70 has a coupling yoke 72 slideably receivable into the cavity 66. The yoke 72 itself has a yoke bore 74 with a central yoke axis 76. The yoke 72 is slidably (and in the embodiments illustrated, rotatably) received within the cavity 66, and disposed to provide that the axis 76 of the yoke 72 is held substantially coaxial with the annulus axis 56 of the housing 42.

In the embodiments illustrated, two yoke linkages 80 pivotably connect the yoke 72 to the housing 42. Although two are shown, it is anticipated that only one such linkage is necessary to provide for satisfactory precision and performance of the coupling mechanism. However, it is clear to one of skill in the art that three or more such linkages could be practiced as well. In the present embodiment, each yoke linkage 80 included a link member 82 connected at a first link end 84 to the yoke 72 by a sliding pivot coupling 86 and at a second end 92 to the housing 42 by a simple pivot coupling 94. The couplings 86 and 94 each have a pivot pin 90. In the simple coupling 94, the pivot pin 90 passes through a clearance aperture 96 in the second end 92 of the link member 82, to be fixedly received in a pivot pin hole(s) 98 in the yoke 72. In the sliding coupling 86, the pivot pin 90 passes through a clearance slot 88 in the first end 84 of the link member 82, to be fixedly received in a pivot pin hole(s) 98 in the housing 42. The pivot pins 90 and pin holes 98 in the illustrated embodiment are friction/wedge fitted together. However, the ordinary skilled artisan knows how to select and substitute other pivot coupling equivalents to these and anticipated by the present invention, such as screw pins and threaded pivot pin holes.

A prosthesis contacting face 100 is disposed on each link member 82. The prosthesis face 100 is disposed to normally interface with a mounting surface 112 of prosthesis component 12 to be secured by the holder 40, and a drift pin 102 is fixed to the link member 82 and projects perpendicularly from the prosthesis face 100 relative to the drift axis 104 of the drift pin 102. The length L that the drift pin extends beyond the prosthesis face 100 is important, and is chosen as noted below.

Figure 4A:
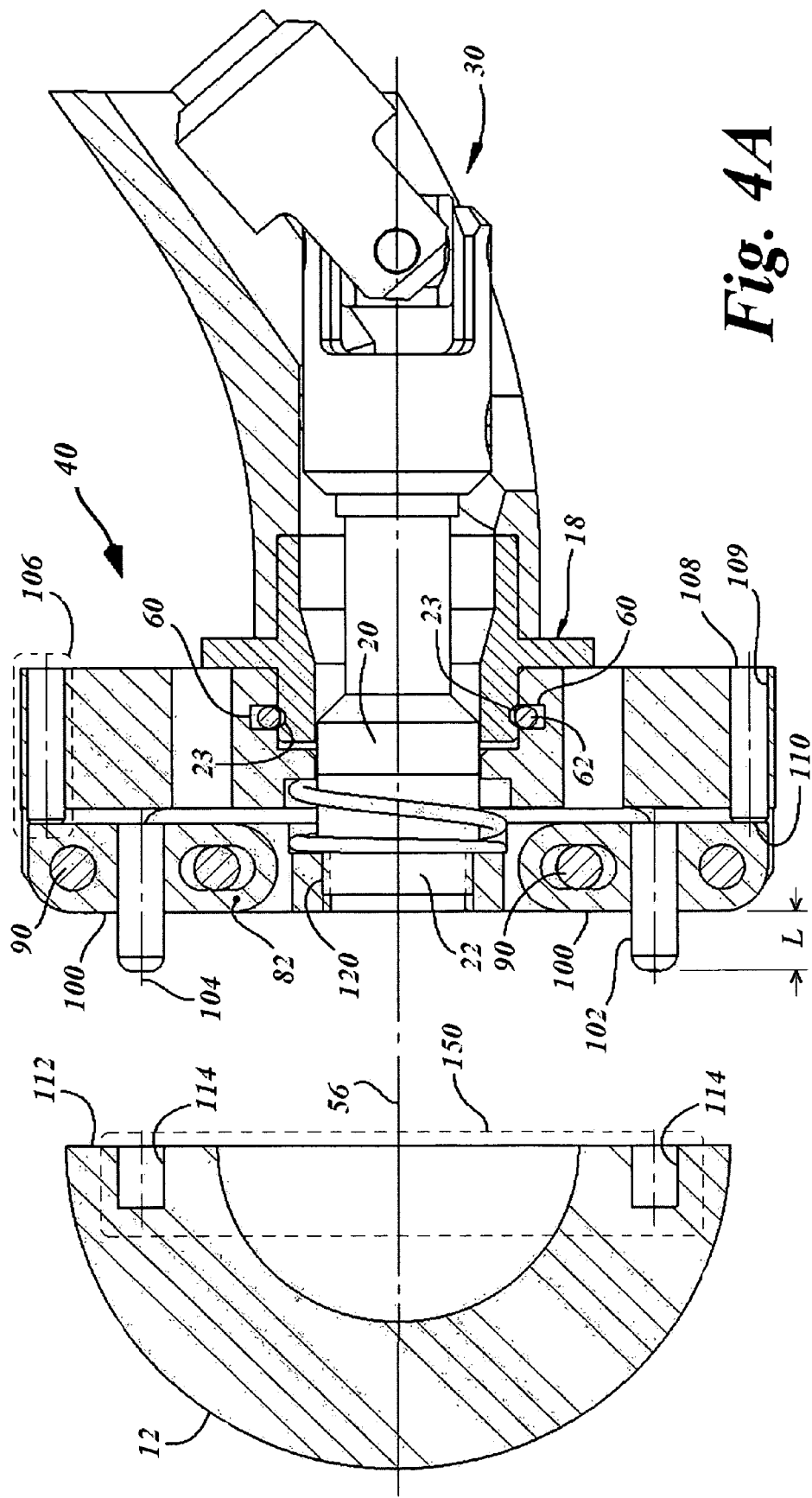
FIG. 4A is a partial cross-sectional view of the present holder mounted to the tool end of an inserter handle with a prosthesis component (a cup insert in the figure) positioned to be attached to the holder.

As illustrated in FIG. 4A, a travel limiter mechanism 106 is associated with at least one yoke linkage 80. In the preferred embodiment illustrated, both linkages 80 had a travel limiter mechanism 106. The travel limiter 106 comprised a limit set pin 108 mounted in the housing 42 proximate the simple pivot coupling 94 and projecting into the coupling toward the second end 92 of the link member 82 to limit the degree of rotation of the link member 82 around the pivot pin 90 of the simple coupling 94. Travel limit is accomplished when the stop seat 110 on the link member 82 contacts the limit set pin 108, preventing the link member 82 from rotating further around the pivot pin 90. Although not shown, the limit set pin 108 can be a set screw received in a threaded set bore 109 (for example, with a locking insert (not shown)). This combination allows the limitation of the degree of rotation of the link member 82 around the pivot pin 90 of the simple coupling 94 to be more readily adjustable than might otherwise be accomplished.

A biasing mechanism 116 is disposed within the cavity 66, and applies a force to the yoke 72 to slide the yoke 72 out of the cavity 66. Although the biasing mechanism 116 in the embodiments illustrated was a single coil helical spring, other biasing mechanisms are anticipated for practice in the present invention. For example, multiple springs or resilient pads can be used. The movement of the yoke 72 out of the cavity 66 acts via the linkages 70 to hold the stop seat 110 of the link member 82 against the limit set pin 108 of the travel limiter 106. By this action, the angular relationship drift axis 104 of the drift pins 102 is set to normally be substantially parallel with each other and with the yoke axis. In this configuration, the drift pins 102 are disposed to be received into drift receivers 114 in the mounting surface 112 of the prosthesis component 12.

Figure 3:
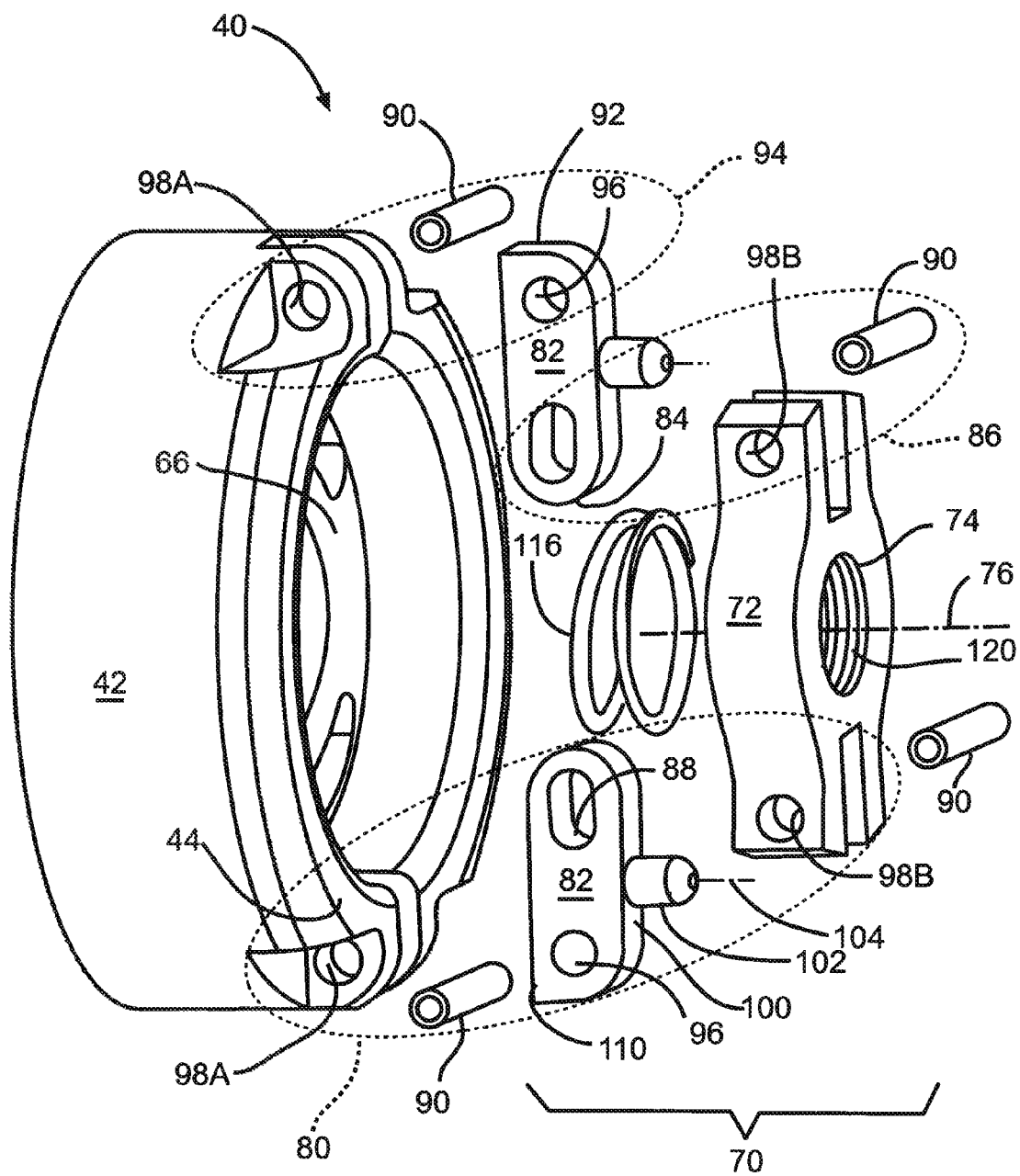
FIG. 3 is an exploded perspective view of components of the present prosthesis component holder.

As shown in FIGS. 3 and 4A, an actuator interface 120 is disposed at the yoke bore 74 of the yoke 72. The actuator interface 120 mechanically connects the coupling mechanism 70 to the draw piston 20 of the inserter handle 10. In the embodiment illustrated, the actuator interface is a threaded receiver in the yoke bore 74 that mates with the threaded interface 22 on the handle draw piston 20 (see FIG. 2). As a result of this arrangement, operation of the draw piston 120 overcomes the normal bias force of the biasing mechanism 116, and draws the yoke 72 of the coupling assembly 70 into the cavity 66. This action causes the link members 82 to rotate on the pivot couplings 94, and concomitantly change the angular relationship of the drift axis 104 drift pins 102 to be progressively more acute (see FIG. 4C), and results in a pincer action of the drift pins 102 in the drift pin receivers 114 of the prosthesis component 12.

Figure 4C:
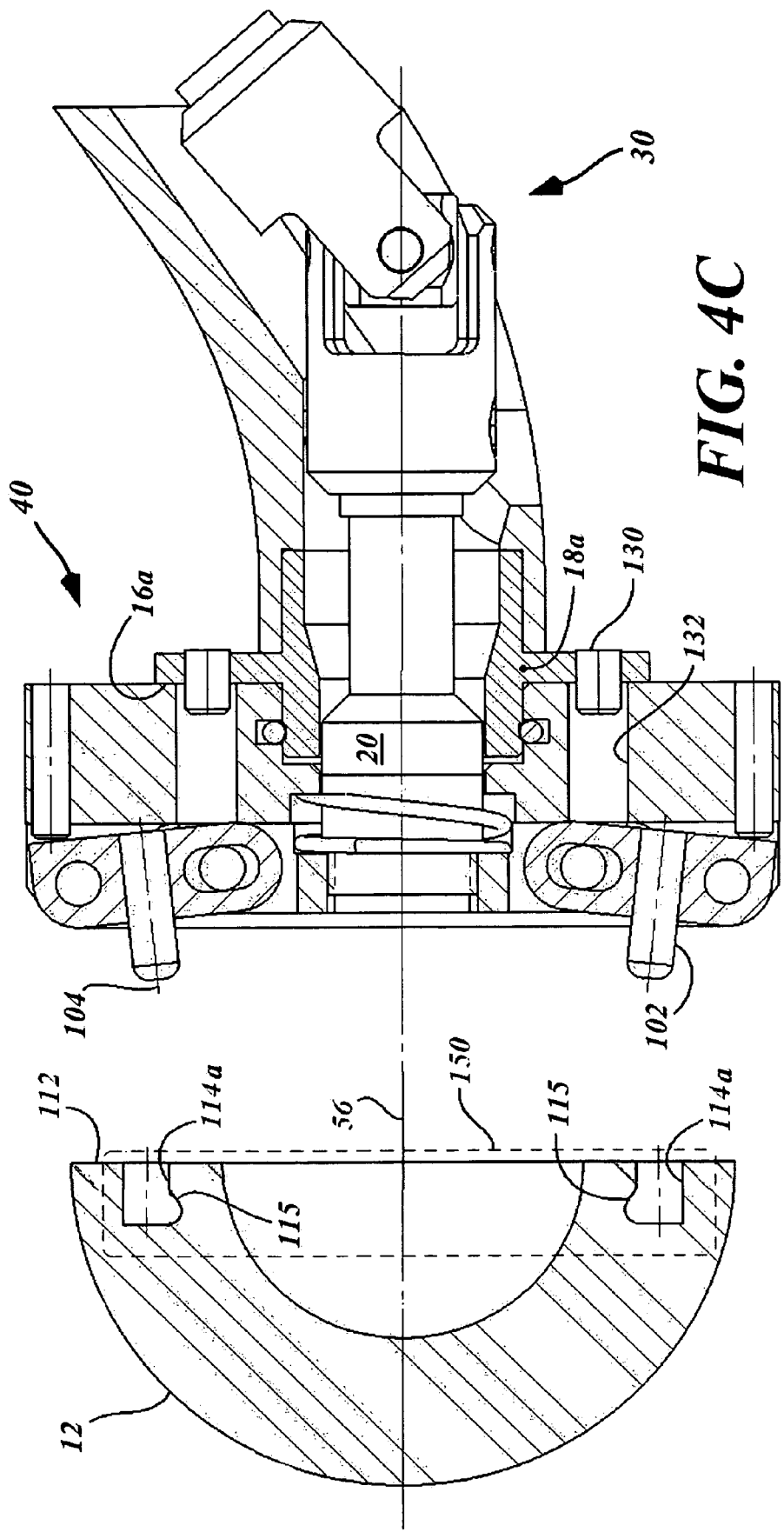
FIG. 4C is a partial cross-sectional view of the present holder mounted to the tool end of an inserter handle after actuation of the holder, and showing the relationship of the component parts of the holder when actuated to secure the prosthesis component in position on the holder.
Figure 4D:
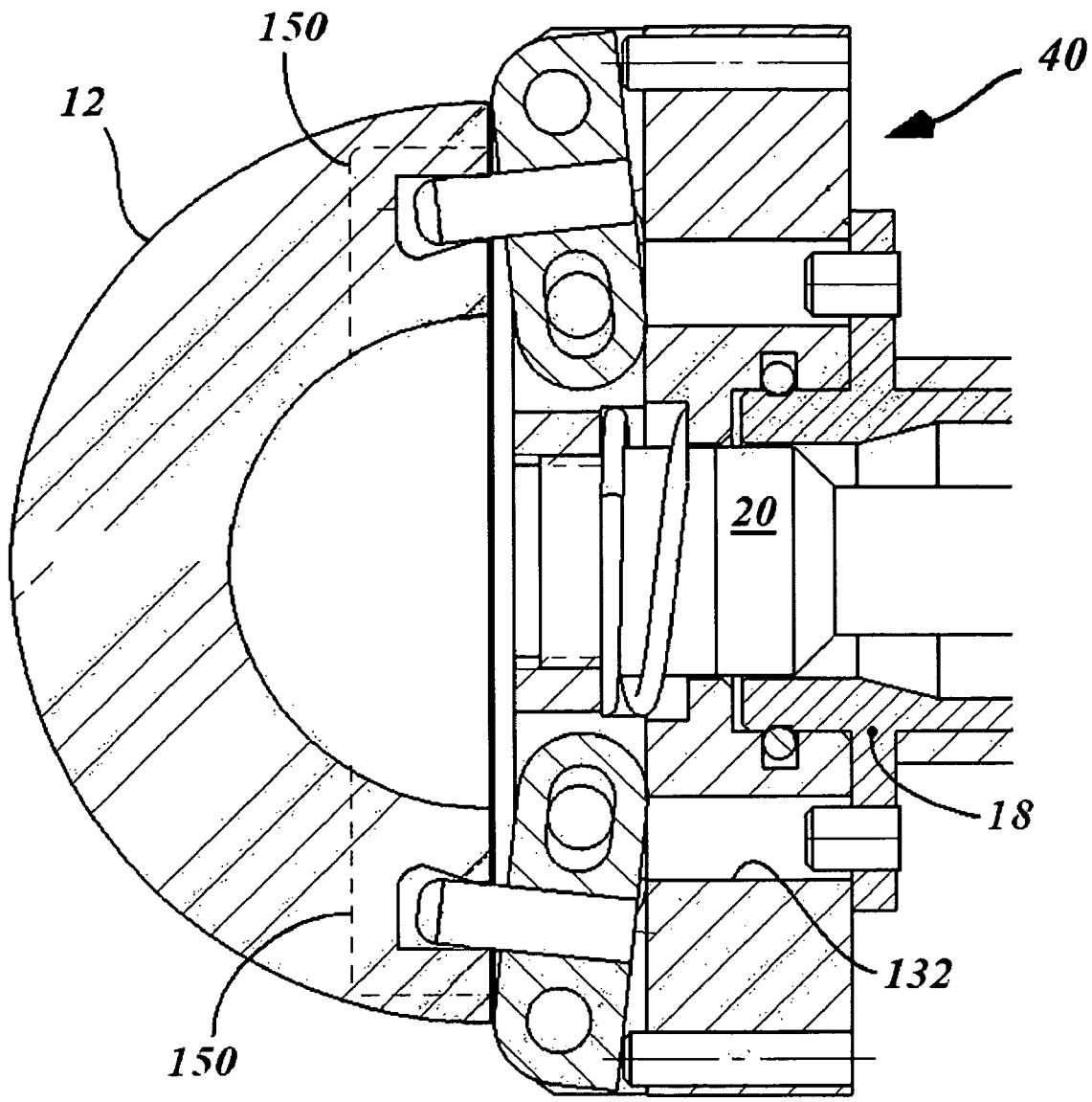
FIG. 4D is a partial cross-sectional view of the present holder mounted to the tool end of an inserter handle with a prosthesis component attached to the holder.

As shown in FIGS. 4C and 4D, when a prosthesis component 12 is positioned on the holder 40 (see FIG. 4B), the pincer action of the drift pins 102 in the drift receivers 114 draws the mounting surface 112 of the component 12 securely against the front surface 44 of the housing 42. Further, the action of drawing the yoke 72 into the cavity 66 applies a force on the housing 42 which drives the back housing surface 46 against the attachment interface 16 of the drive end boss 18 and secures the housing 42 as well to the drive end boss 18 of the inserter handle 10.

FIGS. 4C and 4D also illustrate an alternative configuration of the drift receivers 114a. In this configuration, the receiver 114a has an engagement shoulder 115 to facilitate the pincer action of the drift, pins 102 upon actuation of the holder. A further alternative feature of the present invention illustrated in the figure is the ability to rotate the holder 40 relative to the drive end boss 18 of the inserter handle 10 within a limited range. This is accomplished by the interface surface 16a of the drive end boss 18a having rotation stops 130 projecting from the surface 16a into arcuate limit slots 132 set in the back surface 46 of the housing 42. The radius of the arc of the limit slots 132 corresponds to the radial distance of the rotation stop 130 from the annular axis 56. In this embodiment, once the holder 40 is attached to the drive end boss 18 using the snap-ring and detent attachment mechanism 58 illustrated in the figures, the holder 40 may by rotated within the limits permitted by the interaction of the rotation limit slots 132 with the rotation stops 130. Although, two rotation stops 130 and two limit slots 132 are illustrated, practicing only one stop 130 and one slot 132 is anticipated in the present invention. Additionally, it is anticipated that the combination of one rotation stop 132 is practiced with two rotation limit slots of different arc lengths, to allow a user to select multiple range limits on a single holder 40.

Figure 5A:
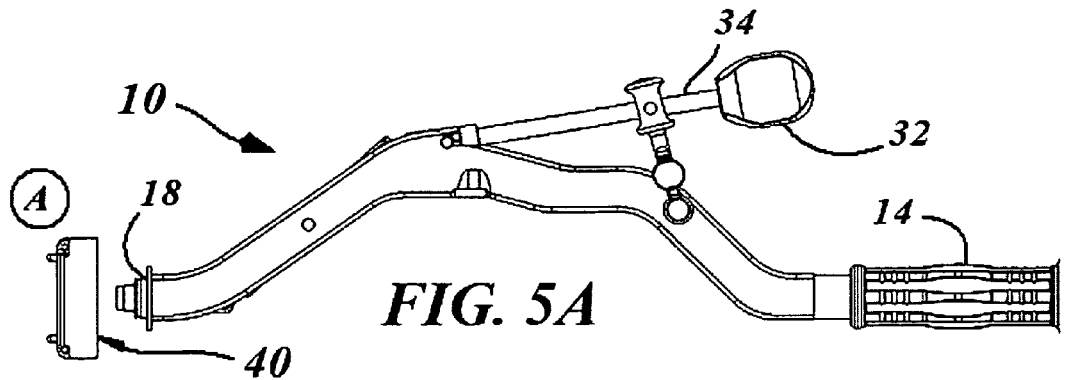
FIGS. 5A to 5C illustrate cooperation of the present holder with an existing inserter handle and (A) attachment of the holder to the inserter handle, (B) interfacing of the draw piston of the inserter handle's drive assembly to the coupling mechanism of the holder, and (C) actuation of the draw piston to secure the prosthesis component to the holder, and the holder to the tool boss of the inserter handle.
Figure 5B:
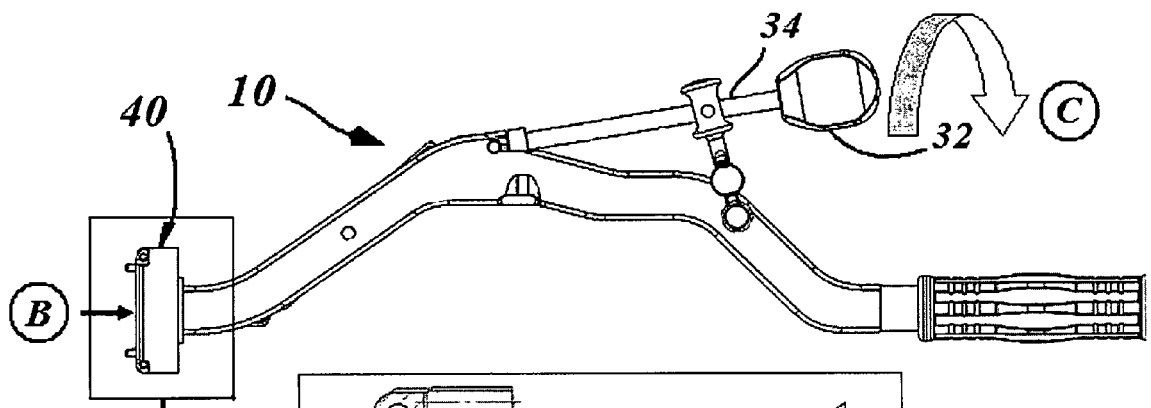
Figure 5B:
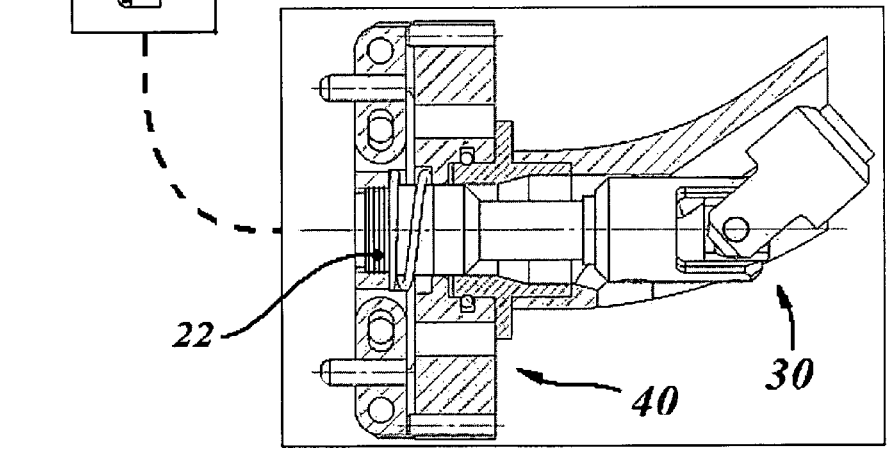
Figure 5C:
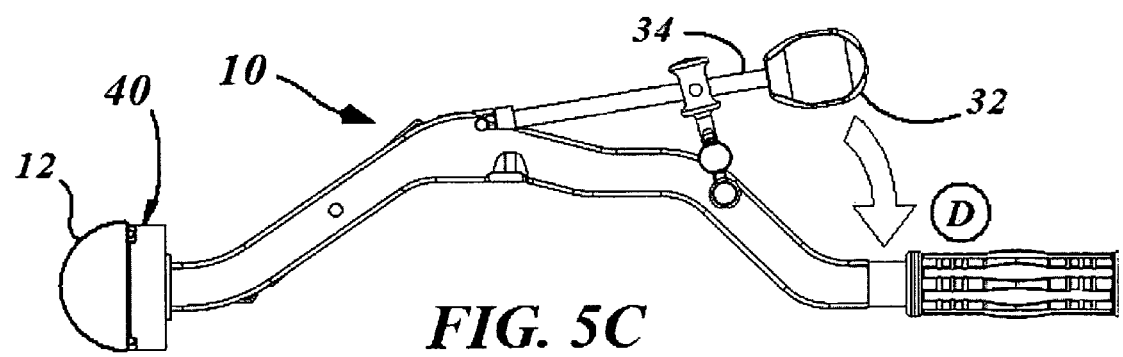

In use, the present holder 40 is attached to the drive end boss 18 of the inserter handle 10. In a first step A as shown in FIG. 5A, the annulus axis 56 is aligned with the draw piston axis 21. Once aligned, the annular opening 54 of the housing 42 is slid over the boss 18 in a second step B until the attachment mechanism 58 engages the complementary mating mechanism 23 on the boss 18. In a third step C, the threaded interface 120 of the yoke 72 is then engaged with the piston threads 22 of the drive piston 20 by rotating the drive knob 32 of the drive train 30. See FIG. 5B. This results in the coupling mechanism 70 of the holder 40 being engage by and in mechanical communication with the drive assembly/linkage 30 of the inserter handle 10.

Once the holder 40 is attached to the drive end boss 18 and engaged with the drive assembly 30, the prosthesis component 12 is positioned on the front surface 44 of the housing 42. In the embodiment illustrated, the prosthesis component 12 is a cup insert as is known in the field. To fully secure the prosthesis component 12 to the holder 40, and in turn, the holder 40 to the boss 18, the drive assembly lever 34 is pushed down and locked to draw the drive piston 20 into the boss 18 in a final step D. This actuates the coupling mechanism 70 of the holder 40 and causes the securing of the component 12 to the holder 40 and the holder 40 to the boss interface 16, as described above.

After the inserter handle 10 with the holder 40 and prosthetic component 12 attached is used to properly position the prosthetic component 12, in situ, in the patient's body, the drive assembly lever 34 is unlocked and released to free the handle 10 and holder 40 combination from the prosthetic component 12. The inserter handle 10 and holder 40 are quickly free from each other by unthreading the draw piston 20 from the holder 40.

An advantage of the present invention is that, once the proper relationship of the prosthetic component is achieved in the installation site, it is not necessary to hold the positional relationship of the inserter handle relative to the installation site during disengagement of the threaded interface of the mount end of the inserter handle from the prosthetic component. An advantage of the present invention is that it allows an existing inserter handle to be quickly disengageable from an attached prosthetic component, and requires little manipulation to accomplish that. An additionally advantage is that the present holder can provide an interface that can accommodate a variety of prosthetic component configurations for combination with a given inserter handle.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiments thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A prosthesis holder that is attachable to an inserter handle, the holder comprising:
   a) a housing attachable to a drive end of an inserter handle, the housing having an opening;
   b) a yoke linkage connecting a yoke to the housing, wherein the yoke comprises a central yoke axis and the yoke linkage comprises a linkage member connected at a first end to the yoke by an articulating pivot coupling comprising a first pivot pin and at a second end to the housing by a simple pivot coupling comprising a second pivot pin, the linkage member comprising a prosthesis face supporting a proximal end of a drift pin having a length extending along a drift pin axis to a drift pin distal end, wherein with the yoke linkage in a distal position, the drift pin axis is substantially parallel to the central yoke axis with the first and second pivot pins residing along a plane perpendicular to the central yoke axis; and c) an actuator interface disposed in a bore of the yoke and being configured to mechanically connect the yoke to a draw piston of an inserter handle, wherein the yoke is movable in a proximal direction against a bias mechanism, thereby causing the yoke linkage to move proximally out of the distal position as the first and second pivot pins move out of the perpendicular plane, the linkage member pivots on the housing and moves the drift pin so that the drift pin axis intersects the central yoke axis at an acute angle having an imaginary focal point distal of the yoke.

2. The holder of claim 1, further comprising:

a) an attachment mechanism disposed on an inner surface of the housing proximate a back surface thereof, the attachment mechanism being configured to releasably attach the housing to a complimentary mating mechanism on a mount end of an inserter handle; and b) a cavity set into a front housing surface of the housing, the cavity communicating with the housing opening and disposed to receive the yoke.

3. The holder of claim 1 comprising at least two yoke linkages connecting the yoke to the housing.

4. The holder of claim 1, further comprising:

a travel limiter associated with the yoke linkage to limit an angular relationship of the drift pin with respect to the central yoke axis from being substantially parallel with respect to each other prior to proximal movement of the yoke out of the distal position to being at the acute angle upon such movement.

5. A prosthesis holder that is attachable to an inserter handle, the holder comprising:

a) an annular housing attachable to a drive end boss of an inserter handle, the annular housing having front, back, outer and inner housing surfaces, the inner housing surface defining an annular opening having an annulus axis;

b) an attachment mechanism disposed on the inner surface of the housing proximate the back surface thereof, the attachment mechanism being configured to releasably mate with a complimentary mating mechanism at a drive end boss of an inserter handle;

c) a cavity set into the front housing surface of the housing, the cavity communicating with the annular opening and disposed to receive a coupling mechanism;

d) the coupling mechanism having a yoke movably receivable into the cavity, the yoke having a yoke bore with a yoke axis being substantially coaxial with the annulus axis, and at least two yoke linkages pivotably connecting the yoke to the housing, each yoke linkage having a link member connected at a first end to the yoke by an articulating pivot coupling and at a second end to the housing by a simple pivot coupling;

e) a prosthesis face disposed on each link member, the prosthesis face disposed to normally interface with a mounting surface of a prosthesis component, and a drift pin fixed to the link member and projecting perpendicularly from the prosthesis face along a drift pin axis;

f) a travel limiter associated with at least one yoke linkage, the travel limiter being a limit set pin mounted in a set pin bore in the housing proximate the simple pivot coupling and projecting toward the second end of the link member of the pivot coupling to limit the degree of rotation of the link member around a pivot pin of the simple pivot coupling when a stop seat on the link member contacts the limit set pin;

g) a bias mechanism disposed within the cavity of the housing to bias the yoke in a direction out of the cavity and acting to hold the stop seat of the link member against the limit set pin, the travel limiter thereby setting the angular relationship of the drift pins to normally be substantially parallel with each other and with the yoke axis and disposed to be received into drift receivers in a mounting surface of a prosthesis; and h) an actuator interface disposed at the yoke bore of the yoke and being configured to mechanically connect the coupling mechanism to a draw piston of an inserter handle, wherein the yoke is moveable in a proximal direction against the bias mechanism and into the housing cavity, thereby causing the link members to rotate on the pivot couplings and to concomitantly change the angular relationship of the drift pins to be progressively more acute.

6. The holder of claim 5, wherein a drive end of the inserter handle has a drive end boss with an interface surface from which a rotation stop perpendicularly projects toward the back surface of the housing into an arcuate rotation limit slot recessed into the back surface, thereby enabling the holder to be rotatable relative to the drive end boss of an inserter handle within a rotation range limited by interaction of the rotation limit slot with the rotation stop.

7. The holder of claim 6, wherein the interface surface has at least two rotation stops perpendicularly projecting toward the back surface of the housing into corresponding arcuate rotation limit slots recessed into the back surface.

8. The holder of claim 6, wherein the interface surface has a single rotation stop perpendicularly projecting toward the back surface of the housing, and the housing has at least two corresponding arcuate rotation limit slots recessed into the back surface which alternatively receive the single rotation stop, the arcuate rotation slots having different lengths to allow a user to select different rotation range limits on a single holder depending on which limit slot the rotation stop is received in.

9. A method for attaching the holder of claim 5 to an inserter handle, comprising the steps of:

a) aligning the annulus axis of the holder with a piston axis of the draw piston at a drive end of an inserter handle;

b) sliding the annular opening of the holder over the drive end boss of the inserter handle until the attachment mechanism of the holder engages the complementary mating mechanism on the drive end boss;

c) engaging a threaded interface of the yoke coupling mechanism with a threaded piston interface of the draw piston by rotating a drive knob of the inserter handle connected to the draw piston via a drive linkage, thereby mechanically engaging the coupling mechanism with the drive linkage of the inserter handle;

d) positioning a prosthesis against the front surface of the holder; and e) manipulating a drive linkage lever to draw the drive piston into the drive end boss to cause the linkage member to pivot on the housing and move the drift pin so that the drift pin axis intersects the central yoke axis at an acute angle, thereby securing the prosthesis to the holder with the holder supported against the boss.

10. A prosthesis holder that is attachable to an inserter handle, the holder comprising:

a) a housing attachable to a drive end of an inserter handle, the housing having an opening;

b) a yoke linkage connecting a yoke to the housing, wherein the yoke comprises a central yoke axis and the yoke linkage comprises a linkage member with a prosthesis face supporting a proximal end of a drift pin extending along a drift pin length to a drift pin distal end, wherein the drift pin length has a drift pin axis that is substantially parallel to the central yoke axis; and c) an actuator interface disposed in a bore of the yoke and being configured to mechanically connect the yoke to a draw piston of an inserter handle, wherein the yoke is movable in a proximal direction against a bias mechanism, thereby causing the linkage member to pivot on the housing and move the drift pin so that the drift pin axis intersects the central yoke axis at an acute angle having an imaginary focal point distal of the yoke, d) wherein the drive end of the inserter handle has drive end boss with an interface surface from which a rotation stop perpendicularly projects toward a back surface of the housing into an arcuate rotation limit slot recessed into the back surface, thereby enabling the holder to be rotatable relative to the drive end boss of an inserter handle within a rotation range limited by interaction of the rotation limit slot with the rotation stop.

11. The holder of claim 1 wherein an attachment mechanism on an inner surface of the housing proximate a back surface thereof is releasably matable with a complimentary mating mechanism at a drive end boss of an inserter handle.

12. The holder of claim 1 wherein a travel limiter comprises a limit set pin mounted in a set pin bore in the housing proximate the simple pivot coupling, the limit set pin projecting toward the second end of the link member of the pivot coupling to limit the degree of rotation of the link member around the second pivot pin of the simple pivot coupling when a stop seat on the link member contacts the limit set pin.

13. The holder of claim 12 wherein the bias mechanism biases the stop seat of the link member against the limit set pin, the travel limiter thereby setting the angular relationship of the drift pin to normally be substantially parallel with the yoke axis with the yoke linkage in the distal position.

14. The holder of claim 1 wherein the housing opening has a housing axis that is substantially co-axial with the yoke axis prior to movement of the draw piston in the proximal direction and wherein movement of the yoke in the proximal direction against the bias mechanism and towards the housing causes the linkage member to pivot on the housing and move the drift pin so that the drift pin axis intersects the housing and central yoke axes at an acute angle.

15. The holder of claim 1 wherein the drive end of the inserter handle has a drive end boss with an interface surface from which a rotation stop perpendicularly projects toward a back surface of the housing into an arcuate rotation limit slot recessed into the back surface, thereby enabling the holder to be rotatable relative to the drive end boss of an inserter handle within a rotation range limited by interaction of the rotation limit slot with the rotation stop.

16. The holder of claim 15 wherein the interface surface has at least two rotation stops perpendicularly projecting toward the back surface of the housing into corresponding arcuate rotation limit slots recessed into the back surface of the housing.

17. The holder of claim 15 wherein the interface surface has a single rotation stop perpendicularly projecting toward the back surface of the housing, and the housing has at least two corresponding arcuate rotation limit slots recessed into the back surface which alternatively receive the single rotation stop, the arcuate rotation slots having different lengths to allow a user to select different rotation range limits on a single holder depending on which limit slot the rotation stop is received in.

18. A prosthesis holder that is attachable to an inserter handle, the holder comprising:

a) a housing having an opening with a housing axis;

b) a yoke linkage connecting a yoke to the housing, wherein the yoke comprises a central yoke axis that is co-axial with the housing axis and the yoke linkage comprises a linkage member connected at a first end to the yoke by an articulating pivot coupling comprising a first pivot pin and at a second end to the housing by a simple pivot coupling comprising a second pivot pin, the linkage member comprising a prosthesis face supporting a drift pin projecting perpendicularly there from along a drift pin axis, wherein with the yoke in a distal position, the drift pin axis is substantially parallel to the housing and central yoke axes and with the first and second pivot, pins residing along a plane perpendicular to the housing and central yoke axes; and c) wherein the yoke is releasably connectable to a draw piston of an inserter handle so that movement of the yoke to a second position closer to the housing than the distal position moves the first and second pivot pins out of the perpendicular plane and causes the linkage member to pivot on the housing and move the drift pin so that the drift pin axis intersects the housing and central yoke axes at an acute angle having an imaginary focal point distal of the yoke.

19. The holder of claim 18 wherein the yoke is biased in the distal position by a bias mechanism positioned between the yoke and the housing.

20. The holder of claim 1 wherein with the yoke moved out of the distal position, the first pivot pin is more proximal than the second pivot pin.

21. The holder of claim 10 wherein the linkage member is connected at a first end to the yoke by an articulating pivot coupling and at a second end to the housing by a simple pivot coupling.

22. A prosthesis holder that is attachable to an inserter handle, the holder comprising:

a) a housing attachable to a drive end of an inserter handle, the housing having an opening;

b) a yoke linkage connecting a yoke to the housing, wherein the yoke comprises a central yoke axis and the yoke linkage comprises a linkage member connected at a first end to the yoke by an articulating pivot coupling comprising a first pivot pin and at a second end to the housing by a simple pivot coupling comprising a second pivot pin, the linkage member comprising a prosthesis face supporting a proximal end of a drift pin having a length extending along a drift pin axis to a drift pin distal end, wherein with the yoke linkage in a distal position, the drift, pin axis is substantially parallel to the central yoke axis;

c) a travel limiter comprising a limit set pin mounted in a set pin bore in the housing proximate the simple pivot coupling, the limit set pin projecting toward an outer surface of the second end of the link member to thereby limit the degree of rotation of the link member around the second pivot pin of the simple pivot coupling when the outer surface of the link member contacts the limit set pin; and d) an actuator interface disposed in a bore of the yoke and being configured to mechanically connect the yoke to a draw piston of an inserter handle, wherein the yoke is movable in a proximal direction against a bias mechanism, thereby causing the yoke linkage to move proximally out of the distal position as the linkage member pivots on the housing and moves the drift pin so that the drift pin axis intersects the central yoke axis at an acute angle having an imaginary focal point distal of the yoke.

23. The holder of claim 22 wherein the limit set pin is threadingly adjustable along the set pin bore in the housing proximate the simple pivot coupling to thereby adjust a length of the set pin extending out beyond the bore.

* * * * *

UNITED STATES PATENT AND TRADEMARK OFFICE
CERTIFICATE OF CORRECTION

PATENT NO. : 8,236,003 B2  
APPLICATION NO. : 11/954379  
DATED : August 7, 2012  
INVENTOR(S) : Jonas Burgi Page 1 of 1

It is certified that error appears in the above-identified patent and that said Letters Patent is hereby corrected as shown below:

On the cover page of Patent 8,236,003, (73) "Greatbatch Medical S.A., Orvi (CH)" should be "Greatbatch Medical S.A., Orvin (CH)".

Signed and Sealed this  
Second Day of October, 2012

David J. Kappos  
*Director of the United States Patent and Trademark Office*